US008748428B2

(12) United States Patent
Schuler et al.

(10) Patent No.: US 8,748,428 B2
(45) Date of Patent: Jun. 10, 2014

(54) USE OF A PKC INHIBITOR

(75) Inventors: Walter Schuler, Grenzach-Wyhlen (DE); Frank P. Stegmeier, Acton, MA (US); Markus Warmuth, Natick, MA (US)

(73) Assignee: Novartis AG, Basel (CH)

( * ) Notice: Subject to any disclaimer, the term of this patent is extended or adjusted under 35 U.S.C. 154(b) by 68 days.

(21) Appl. No.: 13/073,652

(22) Filed: Mar. 28, 2011

(65) Prior Publication Data
US 2011/0245256 A1 Oct. 6, 2011

Related U.S. Application Data

(60) Provisional application No. 61/425,525, filed on Dec. 21, 2010, provisional application No. 61/319,013, filed on Mar. 30, 2010.

(51) Int. Cl.
*A61K 31/495* (2006.01)
(52) U.S. Cl.
USPC ................. 514/249; 514/252.17; 514/414
(58) Field of Classification Search
USPC ................. 514/249, 252.17, 414
See application file for complete search history.

(56) References Cited

U.S. PATENT DOCUMENTS

| | | | |
|---|---|---|---|
| 5,545,636 A | 8/1996 | Heath, Jr. et al. | |
| 5,661,173 A | 8/1997 | Heath, Jr. et al. | |
| 5,668,152 A | 9/1997 | Heath, Jr. et al. | |
| 5,672,618 A | 9/1997 | Heath, Jr. et al. | |
| 5,710,145 A | 1/1998 | Engel et al. | |
| 6,117,861 A | 9/2000 | Engel et al. | |
| 6,645,970 B2 * | 11/2003 | Albert et al. | 514/266.2 |
| 7,220,774 B2 | 5/2007 | Albert et al. | |
| 7,235,555 B2 | 6/2007 | Evenou et al. | |
| 7,358,253 B2 | 4/2008 | Evenou et al. | |
| 7,534,808 B2 | 5/2009 | Evenou et al. | |
| 2008/0318975 A1 | 12/2008 | Wagner et al. | |

FOREIGN PATENT DOCUMENTS

| | | |
|---|---|---|
| EP | 0776895 B1 | 10/1998 |
| EP | 0817627 B1 | 3/2005 |
| EP | 1337527 B1 | 10/2009 |
| EP | 1449529 B1 | 1/2010 |
| WO | 02/38561 A1 | 5/2002 |
| WO | 03/082859 A1 | 10/2003 |
| WO | 2005/041953 A1 | 5/2005 |
| WO | 2007/006533 A2 | 1/2007 |
| WO | 2010/009342 A2 | 1/2010 |

OTHER PUBLICATIONS

Murara et al. CAS: 127: 314506, 1997.*
Harvey et al. CAS: 135: 174678, 2001.*
Nakajima et al. CAS: 141:49693, 2004.*
Su, et al., "PKC-beta controls IkappaB kinase lipid raft recruitment and activation in response to BCR signaling", Nature Immunology, vol. 3, No. 8, pp. 780-786, Aug. 2002.
Rossi et al., "Inhibition of Human Lymphoma cell growth by the PKC-beta selective inhibitor Enzastaurin (LY317615) in combination with multiple therapeutic agents", Blood; Journal of the American Society of Hematology, vol. 112, No. 11, pp. 565-568, 2008.
Rossi et al., "The PKC-beta selective inhibitor, Enzastaurin (LY317615), inhibits growth of Human Lymphoma cells.", Blood; Journal of the American Society of Hematology, vol. 106, No. 11, p. 427, 2005.
Abrams, et al., "B-cell receptor signaling in chronic lymphocytic leukemia cells is regulated by overexpressed active protein kinase C", Blood; Journal of the American Society of Hematology, vol. 109, No. 3, pp. 1193-1201, Feb. 2007.
McCall, et al., "Sotrastaurin. Protein kinase C inhibitor treatment of transplant rejection treatment of psoriasis treatment of uveltis", Drugs of the Future 2009, Prous Science, vol. 34, No. 8, pp. 618-623, Aug. 2009.
Pleyer, et al., "Molecular and cellular mechanisms of CLL: novel therapeutic approaches", Nature Reviews Clinical Oncology, vol. 6, No. 7, pp. 405-418, 2009.
Chen, et al., "Bortezomib overcomes tumor necrosis factor-related apoptosis-inducing ligand resistance in hepatocellular Carcinoma cells in part through the inhibition of the phosphatidylinositol 3-kinase/Akt pathway", Journal of Biological Chemistry, vol. 284, No. 17, pp. 11121-11133, Apr. 2009.
Alizadeh, Ash A. et al., "Distinct Types of Diffuse Large B-Cell Lymphoma Identified by Gene Expression Profiling", Nature, vol. 403, pp. 503-511, 2000.
Apostolidou, Effrosyni et al., "JAK2 Inhibitors: A Reality? A Hope?", Clinical Lymphoma & Myeloma, vol. 9, pp. S340-S345, 2009.
Burns, Christopher J. et al., "Phenylaminopyrimidines as Inhibitors of Janus Kinases (JAKs)", Bioorg. Med. Chem. Lett., vol. 19, pp. 5887-5892, 2009.
Compagno, Mara et al., "Mutations of Multiple Genes Cause Deregulation of NF-kB in Diffuse Large B-Cell Lymphoma", vol. 459, pp. 717-721, 2009.
Davis, Eric R. et al., "Constitutive Nuclear Factor kB Activity is Required for Survival of Activated B Cell-like Diffuse Large B Cell Lymphoma Cells", The Journal of Experimental Medicine, vol. 194, pp. 1861-1874, 2001.
Davis, Eric R. et. al., "Chronic Active B-Cell-Receptor Signalling in Diffuse Large B-Cell Lymphoma", Nature, vol. 463, pp. 88-92, 2010.
Lin, Qiyan et al., "Enantioselective Synthesis of Janus Kinase Inhibitor INCB018424 via an Organocatalytic Aza-Michael Reaction", Org. Lett., vol. 11, No. 9, pp. 1999-2002, 2009.

(Continued)

*Primary Examiner* — Rei-tsang Shiao
(74) *Attorney, Agent, or Firm* — Jennifer Chapman

(57) ABSTRACT

The present invention demonstrates that chronic active BCR signaling through CD79A/B confers a strong dependence on downstream PKCb kinase signaling. Hence, provided herein is a method for inhibiting the growth of B-cell lymphoma having chronic active B-cell-receptor signaling, or inhibiting the growth of cancers with molecular lesions that lead to chronic active BCR signaling, by administering to a patient in need of such treatment a therapeutically effective amount of a PKC inhibitor or a use of a PKC inhibitor to inhibit the growth of B-cell lymphoma having chronic active B-cell-receptor signaling or to inhibit the growth of cancers with molecular lesions that lead to chronic active BCR signaling.

7 Claims, 4 Drawing Sheets

(56) References Cited

OTHER PUBLICATIONS

Naylor, Tara L. et al., "Protein Kinase C Inhibitor Sotrastaurin Selectively Inhibits the Growth of CD79 Mutant Diffuse Large B-Cell Lymphomas", Cancer Res., vol. 71, No. 7, pp. 2643-2653, 2011.

Naylor, Tara et al., "The PKC Inhibitor Sotrastaurin (STN) Selectively Inhibits the Growth of CD79 Mutant Diffuse-Large B-Cell Lymphoma", Apr. 2011 [poster].

Li et al., "Retrospective analysis of protein kinase C-beta (PKC-beta) expresiion in lymphoid malignancies and its association with survival in diffuse large B-cell lymphomas", Biology Direct, 2:8, (2007); http://www.biology-direct.cpm/conent/2/1/8.

Obrador-Hevia et al., "Molecular Biology of mantle cell lymphona: From profiling studies to new therapeutic strategies", Blood Reviews, vol. 23, pp. 205-216, (2009).

* cited by examiner

USE OF A PKC INHIBITOR

FIELD OF THE INVENTION

The present invention relates to the use of PKC inhibitors for inhibiting the growth of B-cell lymphomas having chronic active B-cell-receptor signaling, in particular CD79 mutant diffuse-large B-cell lymphomas.

BACKGROUND

Diffuse large B cell lymphoma (DLBCL) is the most common form of malignant lymphoma and is diagnosed in over 20,000 patients each year in the US. DLBCL is heterogeneous with respect to morphology, biology, and clinical presentation. By gene expression profiling, at least three molecular subtypes of DLBCL can be distinguished termed Germinal center B cell-like (GC) DLBCL, activated B cell-like (ABC) DLBCL, and primary mediastinal B-cell lymphoma (PMBL). See Alizadeh, A. A., et al, Nature 403(6769), 503-522 (2000). The molecular DLBCL subtypes however differ not only with respect to the expression of thousands of genes, but also have significantly different overall survival rates. GCB DLBCL and PMBL patients respond favorably to conventional treatment. In contrast, ABC DLBCL represents the least curable subtype with 3-year overall survival rates of only 40% following combined therapy with anti-CD20 antibody Rituximab and chemotherapy for the treatment of non-Hodgkin lymphoma (CHOP) regimen or (R-CHOP). In addition, each subtype is characterized by deregulation of distinct oncogenic pathways. ABC DLBCL, for example, is characterized by constitutive nuclear factor-KB (NF-κB) pathway activation predominantly via the CBM (CARD11/BCL10/MALT1) signaling complex, which promotes cell proliferation, differentiation and suppresses apoptosis. See Davis, R. E., et al., *J Exp Med*, 194(12), 1861-1874 (2001).

Physiologically, activation of the CBM complex in B-cells occurs in response to B-cell receptor (BCR) stimulation. Antigen-binding to the BCR induces receptor oligomerization, which promotes Lyn-mediated phosphorylation of immunoreceptor tyrosine-based activation motifs (ITAM) domains in the B-cell coreceptors CD79A and CD79B. Phosphorylated ITAM domains recruit and activate the spleen tyrosine kinase (SYK) at the plasma membrane, which initiates downstream signaling through Bruton's tyrosine kinase (BTK) and phospholipase C gamma (PLCλ) and ultimately leads to the activation of protein kinase C (PKC). PKCβ is thought to be the predominant PKC isoform mediating BCR-NF-κB activation in B-cells through phosphorylation of the Caspase recruitment domain-containing protein 11 (CARD11, also known as CARMA1). The phosphorylation of the CARD11 linker domain leads to a conformational change that promotes CBM complex assembly. Once activated at the plasma membrane, the CBM complex facilitates the activation of the IKK (I kappa B kinase) complex, which phosphorylates IκBα targeting it for destruction, and thereby allows NF-κB transcription factors to enter the nucleus and drive the expression of NF-κB target genes. While it was long unclear whether NF-κB activation in ABC DLBCL merely reflects the signaling state of the tumor cell of origin, the identification of oncogenic CARD11 mutations in this subtype provided the first evidence for genetic deregulation of this pathway. See Lenz, G., et al, *Science* 319(5870), 1676-9 (2008). In addition, more recent studies have revealed somatically acquired tumor lesions in several NF-κB pathway regulators, including frequent loss-of function mutations in the negative regulator A20 and genetic abnormalities in CD79A and CD79B. See. e.g., Compagno, M., et al, "Mutations of multiple genes cause deregulation of NF-κB in diffuse large B-cell lymphoma" *Nature*, 459 (7247), 717-722 (2009); Davis, E. R., et al., "Chronic active B-cell-receptor signalling in diffuse large B-cell lymphoma" *Nature*, 463, 88-94 (2010)). Thus, it is likely that most, if not all, ABC DLBCL may harbor genetic lesions that constitutively activate NF-κB pathway signaling.

Previous studies showed that ABC DLBCL lines are sensitive to inhibition of CARD11, BCL10, MALT1, or IKKβ, demonstrating a clear dependence on NF-κB pathway signaling. See Ngo, V. N., et al. *Nature* 441(7089):106-10 (2006). In addition, Davis et al. reported dependency of ABC DLBCL cell lines with wildtype CARD11 on BCR signaling and demonstrated that inhibition of CD79A resulted in cell death. See, Davis et al., *Nature*, 463, 88-94 (2010). These results contrast a recent study which proposed that ligand-independent 'tonic' BCR signaling is a more general feature of B-cell lymphomas that renders these cells dependent on downstream BCR signaling. See Chen, L., et al. *Blood* 111(4): 2230-7 (2008).

SUMMARY

The present invention demonstrates that chronic active BCR signaling through CD79A/B confers a strong dependence on downstream PKCβ kinase signaling.

Hence, in one embodiment, the present invention provides a method for inhibiting the growth of B-cell lymphoma having chronic active B-cell-receptor signaling (preferably, a CD79 mutant diffuse-large B-cell lymphoma, in particular cancers with CD79A/B mutations (e.g., non-Hodgkin's lymphoma)) by administering to a patient in need of such treatment a PKC inhibitor (preferably, a selective PKC alpha/beta inhibitor).

In another embodiment, the use of a PKC inhibitor (preferably, a selective PKC alpha/beta inhibitor) to inhibit the growth of B-cell lymphoma having chronic active B-cell-receptor signaling (preferably, a CD79 mutant diffuse-large B-cell lymphoma, in particular cancers with CD79A/B mutations (e.g., non-Hodgkin's lymphoma)) is provided.

Another aspect of the present invention provides a method for inhibiting the growth of B-cell lymphoma having chronic active B-cell-receptor signaling (preferably, a CD79 mutant diffuse-large B-cell lymphoma, in particular cancers with CD79A/B mutations (e.g., non-Hodgkin's lymphoma)) by administering to a patient in need of such treatment a PKC inhibitor (preferably, a selective PKC alpha/beta inhibitor) in combination with an additional pharmaceutical agent (as described herein below). In one embodiment, the use of a PKC inhibitor (preferably, a selective PKC alpha/beta inhibitor) in combination with an additional pharmaceutical agent (described herein below) to inhibit the growth of B-cell lymphoma having chronic active B-cell-receptor signaling (preferably, a CD79 mutant diffuse-large B-cell lymphoma, in particular cancers with CD79A/B mutations (e.g., non-Hodgkin's lymphoma)) is provided.

The combination therapies described above may be administered as (a) a single pharmaceutical composition which comprises a PKC inhibitor (preferably, a selective PKC alpha/beta inhibitor), at least one additional pharmaceutical agent, and a pharmaceutically acceptable carrier; or (b) two separate pharmaceutical compositions comprising (i) a first composition comprising a PKC inhibitor (preferably, a selective PKC alpha/beta inhibitor) and a pharmaceutically acceptable carrier, and (ii) a second composition comprising at least one additional pharmaceutical agent and a pharmaceutically acceptable carrier. The pharmaceutical compositions may be administered simultaneously or sequentially and in any order. Preferably, the additional pharmaceutical agent is a mTOR inhibitor, a PI3K inhibitor, or a JAK inhibitor. In one embodiment, the PKC inhibitor (preferably, a selective PKC alpha/beta inhibitor) is combined with a mTOR inhibitor. In another embodiment, the PKC inhibitor (preferably, a selective PKC alpha/beta inhibitor) is combined with a PI3K inhibitor. In yet another embodiment the PKC inhibitor (preferably, a selective PKC alpha/beta inhibitor) is combined with a JAK inhibitor (preferably, a selective JAK2 inhibitor, selective JAK1 and/or JAK2 inhibitor, selective JAK1 and/or JAK3 inhibitor, or selective JAK2 and/or TYK2 inhibitor).

DEFINITIONS

As used herein, the term "PKC inhibitor" refers to a protein kinase C inhibitor that may be pan (multi-subtype) or selective to one or more PKC isozymes. The term PKC generally refers to the entire family of isoforms: conventional isoforms; alpha, beta ($\beta1$ and $\beta2$) and gamma, novel isoforms; delta, epsilon, eta, and theta, and atypical isoforms; zeta, and tau/lambda.

The term "selective PKC inhibitor" refers to a PKC inhibitor that possesses a selectivity of at least about 20 fold for one or more PKC isoforms as compared to the other PKC isoforms. Preferably, the selectivity is at least about 100 fold, more preferably at least about 500 fold, most preferably at least about 1,000 or at least about 2,000 fold.

The term "selective PKC alpha/beta inhibitor", "selective PKC $\alpha/\beta$ inhibitor" or "selective PKCa/b inhibitor" refers to a protein kinase C inhibitor that is more selective for the alpha and/or beta PKC isoform of PKC than the other isoforms of PKC. For example, PKC alpha or PKC alpha and beta, over the other PKC isoforms of at least about 20 fold (preferably at least about 100, more preferably at least about 500, most preferably at least about 1,000 or at least about 2,000 fold).

DETAILED DESCRIPTION

Figure 1:
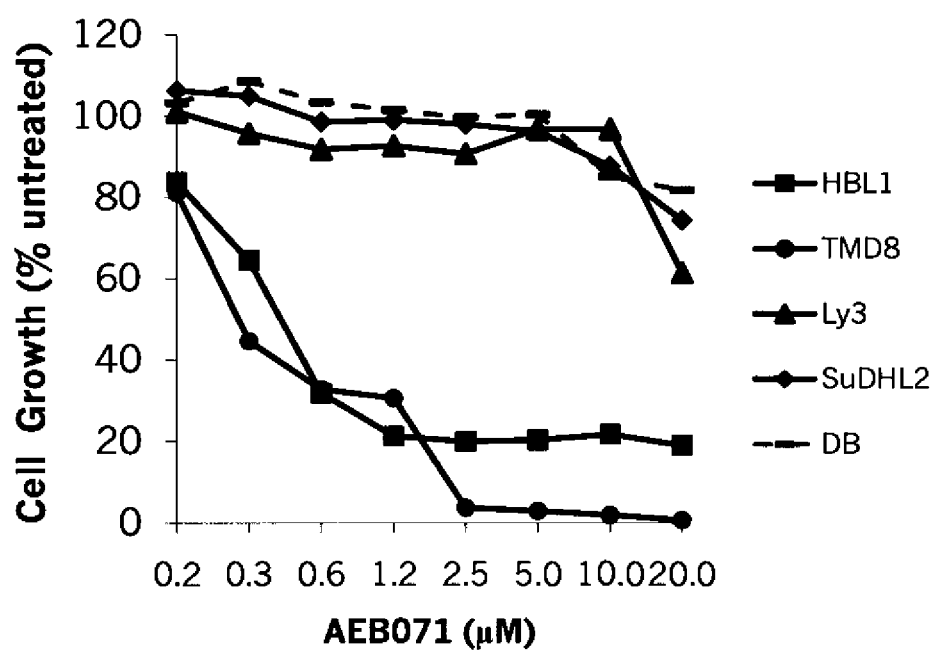
FIG. 1 illustrates the growth inhibitory effect of AEB071 (pan-PKC inhibitor) over a concentration range of 0.16 μM to 20 μM, where relative cell growth is expressed as a percentage of cells treated with DMSO.

PKC inhibitors useful in the practice of the present invention may inhibit several isoforms of the PKC, in particular they may selectively inhibit specific PKC isoforms (e.g., selective PKC inhibitors or isozyme-selective PKC inhibitors). Preferably, the PKC inhibitors are able to selectively inhibit PKC isoforms which are selected from the classical PKC isoforms ($\alpha$, $\beta1$, $\beta2$, $\gamma$) and novel PKC isoforms ($\epsilon$, $\eta$, $\delta$, $\theta$) or atypical isoforms ($\zeta$, $\tau/\lambda$), more preferably selected from the $\alpha$, $\beta$ ($\beta1$ and $\beta2$ isoforms) and $\theta$ PKC isoforms. Preferred PKC inhibitors are able to selectively inhibit the $\alpha$ and $\beta$ isoforms. Suitable PKC inhibitors include maleimide derivatives, such as compounds described in U.S. Pat. Nos. 5,545,636; 5,668,152; 5,672,681; 5,698,578; 5,710,145; 6,645,970; 7,220,774; 7,235,555; US Publication No. 2008/0318975; European Patent Nos. 0776895 B1; 0817627 B1; 1449529 B1; 1337527 B1; and PCT Publication Nos. WO03/082859; and WO07/006,533. Each of the references cited above are incorporated herein by reference.

Specific compounds of interest include sotrastaurin (also known as AEB071 and described in U.S. Pat. No. 6,645,970), 3-(1H-Indol-3-yl)-4-[2-(piperazin-1-yl)quinazolin-4-yl]-1H-pyrrole-2,5-dione (described in U.S. Pat. No. 6,645,970), 3-[2-chloro-7-[(dimethylamino)methyl]-1-naphthalenyl]-4-[7-[2-(2-methoxyethoxy)ethoxy]-1H-indol-3-yl]-1H-pyrrole-2,5-dione (described in PCT Publication No. WO07/006,533 and US Publication No. 2008/0318975), 3-[3-(4,7-diaza-spiro[2,5]oct-7-yl)-isoquinolin-1-yl]-4-(7-methyl-1H-indol-3-yl)-pyrrole-2,5-dione (described in Example 69 of U.S. Pat. No. 7,235,555); ruboxistaurin ((9S)-9-[(dimethylamino)methyl]-6,7,10,11-tetrahydro-9H,18H-5, 21:12,17-dimethenodibenzo-[e,k]pyrrolo[3,4-h][1,4,13]oxadiazacyclohexadecine-18,20(19H)-dione (also known as LY-333531 and described in U.S. Pat. No. 5,698,578)) and the mesylate salt of ruboxistaurin (described in European patent No. 0776895 B1). Each of the references cited above are incorporated herein by reference.

Suitable selective PKCα/β inhibitors include 3-[2-chloro-7-[(dimethylamino)methyl]-1-naphthalenyl]-4-[7-[2-(2-methoxyethoxy)ethoxy]-1H-indol-3-yl]-1H-pyrrole-2,5-dione (CAS No. 919992-85-1 described in PCT Publication No. WO07/006,533 and US Publication No. 2008/0318975); 3-(1H-indol-3-yl)-4-[2-(piperazin-1-yl)quinazolin-4-yl]pyrrole-2,5-dione having the following structure and described in Example 70 of PCT Publication No. WO 2002/038561 or U.S. Pat. No. 6,645,970; (9S)-9-[(dimethylamino)methyl]-6,7,10,11-tetrahydro-9H,18H-5, 21:12,17-dimethenodibenzo-[e,k]pyrrolo[3,4-h][1,4,13]oxadiazacyclohexadecine-18,20(19H)-dione (also referred to as ruboxistaurin or LY-333531, CAS No. 169939-94-0 described in U.S. Pat. No. 5,698,578); ruboxistaurin mesylate salt (described in U.S. Pat. No. 5,710,145 and EP Patent No. 776895 B1); and 12-(2-cyanoethyl)-6,7,12,13-tetrahydro-13-methyl-5-oxo-5H-indolo(2,3-a) pyrrolo(3,4-c)-carbazole (CAS No. 136194-77-9, available from Calbiochem® and described in U.S. Pat. No. 5,489,608).

Alternative ways of inhibiting PKC activity are through the use of nucleid acid strategies, such as antisense or small interfering RNAs (siRNAs) directed either at one or multiple PKC isoforms (e.g., the PKC-α antisense oligonucleotide, aprinocarsen (also known as ISIS 3521/LY900003)).

The following compounds were used in the experiments described below and are either available from commercial sources (e.g., Calbiochem®) or prepared using the preparation described in the corresponding reference(s) cited herein below.

Compound A (IKKb inhibitor)-control: N-[(2R,6R)-2,6-dimethyl-4-piperidinyl]-4-(7-fluoro-1H-indol-3-yl)-2-pyrimidinamine (CAS No. 778646-25-6) described in U.S. Pat. No. 7,615,562, incorporated herein by reference.

Compound A

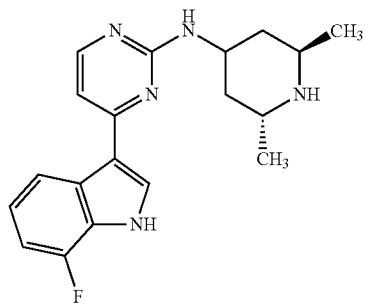

MLN120B (IKKb inhibitor)-control: N-(6-chloro-7-methoxy-9H-β-carbolin-8-yl)-2-methylnicotinamide (CAS No. 783348-36-7) described in PCT Publication No. WO04/092167 and US Publication No. 2004/0235839.

MLN120B

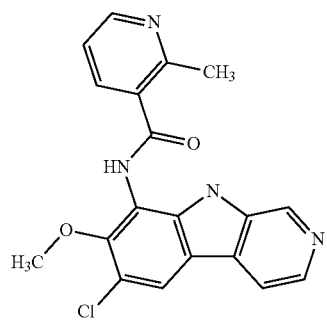

Sotrastaurin: 3-(1H-Indol-3-yl)-4-[2-(4-methylpiperazin-1-yl)quinazolin-4-yl]-1H-pyrrole-2,5-dione (AEB-071, CAS No. 425637-18-9) described in *Drugs of the Future*, 34(8), pp 618-623 (2009) and U.S. Pat. No. 6,645,970, incorporated herein by reference.

AEB-071

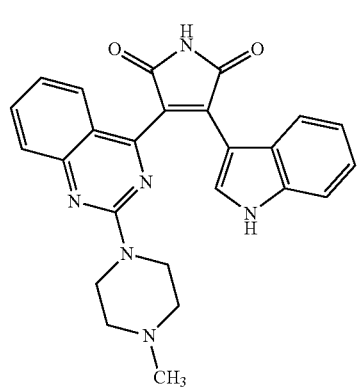

Compound B: 3-[2-chloro-7-[(dimethylamino)methyl]-1-naphthalenyl]-4-[7-[2-(2-methoxyethoxy)ethoxy]-1H-indol-3-yl]-1H-Pyrrole-2,5-dione (CAS No. 919992-85-1) described in PCT Publication No. WO07/006,533 and US Publication No. 2008/0318975, incorporated herein by reference.

(Compound B)

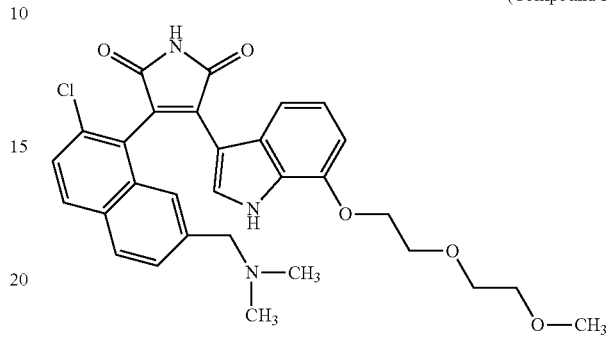

Compound C: 3-[3-(4,7-diaza-spiro[2,5]oct-7-yl)-isoquinolin-1-yl]-4-(7-methyl-1H-indol-3-yl)-pyrrole-2,5-dione having the following structure and described in Example 69 of U.S. Pat. No. 7,235,555.

(Compound C)

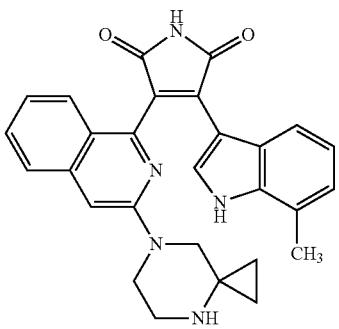

Compound D: 3-(1H-Indol-3-yl)-4-[2-(piperazin-1-yl)quinazolin-4-yl]pyrrole-2,5-dione having the following structure and described in Example 70 of PCT Publication No. WO 2002/038561 or U.S. Pat. No. 6,645,970.

(Compound D)

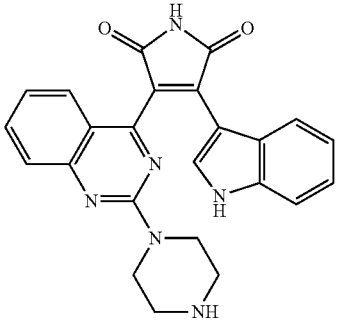

Ruboxistaurin: (9S)-9-[(dimethylamino)methyl]-6,7,10,11-tetrahydro-9H,18H-5, 21:12,17-dimethenodibenzo[e,k]pyrrolo[3,4-h][1,4,13]oxadiazacyclohexadecine-18,20(19H)-dione, (LY-333531, CAS No. 169939-94-0) having the following structure and described in U.S. Pat. No. 5,698,578, incorporated herein by reference, and mesylate salt in EP Patent No. 776895 B1.

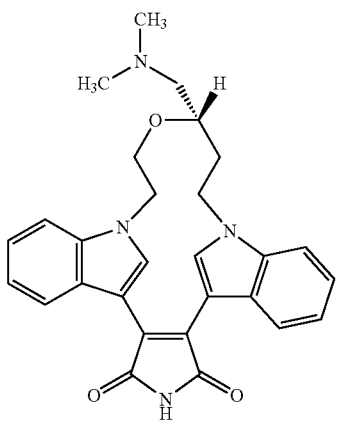

LY-333531

The PKC inhibition activity of the PKC inhibitors may be determined in an Allogeneic Mixed Lymphocyte Reaction (MLR) assay. MLR assay can be done according to methods known to those of skill in the art, e.g., mouse or human MLR assay described in European Publication No. 1337527 A1.

In a preferred embodiment, the PKC inhibitors show an $IC_{50}$ value of less than about 1 µM, preferably less than about 10 nM in the MLR assay.

Davis et al. identified mutations in the BCR co-receptor CD79A/B that lead to chronic activation of BCR signaling. See, Davis, R. E., "Chronic active B-cell-receptor signalling in diffuse large B-cell lymphoma" Nature, 463 (7277), 88-94 (2010). To test for the utility of PKC inhibitors in treating B cell lymphomas, the effects of PKC inhibitors were evaluated on a panel of B cell lymphoma cell lines. DLBCL cell lines of the GC and ABC subtypes were included and confirmed that three ABC DLBCL cell lines (OCI-Ly10, HBL1, and TMD8) harbor mutations in the ITAM motif of CD79A/B. See Davis, E. R., et al., "Chronic active B-cell-receptor signalling in diffuse large B-cell lymphoma" Nature, 463, 88-94 (2010)).

Two pharmacological PKC inhibitors: (i) the pan-PKC inhibitor, Sotrastaurin, also known as AEB071, and (ii) the PKCa/b-selective compound, 3-[2-chloro-7-[(dimethylamino)methyl]-1-naphthalenyl]-4-[7-[2-(2-methoxyethoxy)ethoxy]-1H-indol-3-yl]-1H-pyrrole-2,5-dione (referred to herein as "Compound B"), were used to evaluate the proliferation of several diffuse large B cell lymphoma (DL-BCL) lines. The IKKb-selective inhibitors N-(6-chloro-7-methoxy-9H-β-carbolin-8-yl)-2-methylnicotinamide (referred to herein as "MLN120B") and N-[(2R,6R)-2,6-dimethyl-4-piperidinyl]-4-(7-fluoro-1H-indol-3-yl)-2-pyrimidinamine (referred to herein as "Compound A") were used as control compounds. ABC DLBCL cell lines (OCI-LY3, OCI-LY10, HBL1, U2932, TMD8, Su-DHL2) and GC DLBCL cell lines (Su-DHL4, DB, K-422) were treated for 5 days with PKC inhibitors (A) Sotrastaurin (AEB071) or (B) Compound B; IKKb inhibitors (C) MLN120B or (D) Compound A. Cells were plated in 96-well plates (Corning, #3358) at 5000 cells/well in 100 µL and treated with DMSO or inhibitors at concentrations ranging from 160 nM to 20 µM (2-fold dilutions). Following 5 days of treatment, cells were lysed with CellTiter-Glo® Luminescent Cell Viability Assay reagent (Promega, G7573), lysates were transferred to opaque 96-well plates (Corning, #3971), and luminescence signal was read using the Envision. Percent growth was calculated relative to median DMSO signal.

GC subtype cells were generally insensitive to both IKK and PKC inhibitors, with a half-maximal growth inhibitory concentration ($IC_{50}$) greater than 10 µM in Su-DHL4 and DB cells, which is consistent with the notion that this subtype does not have deregulated NFkB pathway activation (Table 1B below). While all ABC DLBCL cell lines were sensitive to IKK inhibitors, their response to PKC inhibitors varied strongly (Table 1A below). The cell lines that are insensitive to PKC inhibitors, OCI-Ly3 and Su-DHL2, have reported mutations in CARD11 and A20, respectively. Both of these cell lines exhibited $IC_{50}$ values greater than 10 µM in the growth assays with the PKC inhibitors despite being sensitive to IKKβ inhibition (FIG. 1 and Table 1A below). The fact that these oncogenic lesions are thought to function downstream of PKCβ in CBM-NFkB signaling provides a molecular rationale for their insensitivity. U2932 cells, which displayed intermediate sensitivity to PKC inhibitors (Table 1A below) were recently reported to harbor TAK1 mutations, although their oncogenic nature has not yet been confirmed experimentally. See, Compagno, M., et al, "Mutations of multiple genes cause deregulation of NF-κB in diffuse large B-cell lymphoma" Nature, 459 (7247), 717-722 (2009)). In contrast, HBL1, TMD8, and OCI-Ly10 cells, which were confirmed to have CD79A/B mutations, were very sensitive to both PKC inhibitors, with $IC_{50}$ values ranging from 0.2-1.0 µM (FIG. 1A,B), indicating that these cell lines are dependent on BCR signal transduction upstream of CARD11. Tables 1A and 1B below show the growth inhibitory $IC_{50}$ values, which were determined by measuring ATP concentration (Cell Titer Glo), for the indicated compounds in the indicated cell lines. $IC_{50}$ values were determined as the concentration of compound that leads to 50% reduction of cell growth. Representative curves of the primary data for AEB071 are displayed in FIG. 1. ND indicates that $IC_{50}$ value was not determined for that compound.

TABLE 1A

| | | ABC | | | | | |
|---|---|---|---|---|---|---|---|
| | NFkB mutation | CD79A | CD79B | CD79B | TAK1 | A20 | CARD11 |
| Target | Compound | OCI-Ly10 | HBL1 | TMD8 | U2392 | Su-DHL2 | OCI-Ly3 |
| PKCb | AEB071 | 1.3 | 0.5 | 0.2 | 5 | >20 | >20 |
| | Compound D | ND | 0.2 | 0.2 | 3 | >20 | 15 |
| | Compound B | 0.5 | 0.5 | 0.2 | 10 | 15 | >20 |
| IKKb | Compound A | 0.3 | 2.5 | 0.2 | 2.5 | 15 | 0.4 |
| | MLN120B | 10 | 10 | 10 | 10 | 10 | 12 |

TABLE 1B

| | GC | | |
|---|---|---|---|
| NFkB mutation | none | none | none |
| Target | Compound | Su-DHL4 | DB | K422 |
| PKCb | AEB071 | >20 | >20 | >20 |
| | Compound D | 15 | >20 | ND |
| | Compound B | 7.5 | >20 | 11 |
| IKKb | Compound A | 10 | >20 | 10 |
| | MLN120B | >20 | >40 | >40 |

The present invention demonstrates that chronic active BCR signaling through CD79A/B confers a strong dependence on the catalytic activity of PKC and demonstrates the utility of pan-PKC or PKCa/b selective inhibitors to inhibit the growth of cancers with molecular lesions that lead to chronic active BCR signaling.

Reduction of NFkB Pathway Signaling in CD79 Mutant Cells with PKC Inhibitors:

Constitutive activation of the NFkB pathway is a molecular hallmark of ABC DLBCL cells and is required for their proliferation and survival. See Davis, R. E., et al., *J Exp Med*, 194(12), 1861-1874 (2001). To confirm that the growth inhibitory effect in response to PKC inhibition is mediated through modulation of NFkB pathway signaling, the expression of NFkB pathway genes were monitored in response to AEB071 treatment. The NFkB-pathway-induced cytokine IL-6 was used as a marker to study NFkB pathway modulation by PKC inhibitors. See Lam, L. T., et al., *Blood* 111(7): 3701-13 (2008). To measure IL-6 mRNA levels, cells were plated in E-well plates in 2 ml media at 2M/ml, then treated with DMSO or inhibitors from 10 nM to 10 uM (4-fold dilutions) for 24 hours. Total RNA was harvested using the RNeasy kit (Qiagen, #74104) and cDNA was made from 1 μg total RNA using the High Capacity cDNA kit (ABI, #4368814), according to manufacturer's protocols. Taqman probes (ABI: IL-6, Hs00174131_m1) were used with Gene Expression Master Mix (ABI, 4369510) to determine the amount of mRNA expression for IL-6 relative to an endogenous control gene (ABI: TBP, 4326322E) and the DMSO control using the delta-delta $C_t$ method. AEB071 treatment resulted in a dose-dependent decrease in IL-6 mRNA expression in the CD79 mutant cell lines OCI-Ly10, HBL1 and TMD8; whereas, IL-6 mRNA expression was unaffected in the mutant CARD11 cell line OCI-Ly3 (FIG. 2A). The TMD8 cells were then treated with two additional PKC inhibitors (Compound B and LY333531), which also reduced IL-6 mRNA expression in a dose-dependent manner, demonstrating that IL-6 modulation is an on-target effect of PKC inhibition (FIG. 2B).

Figure 2:
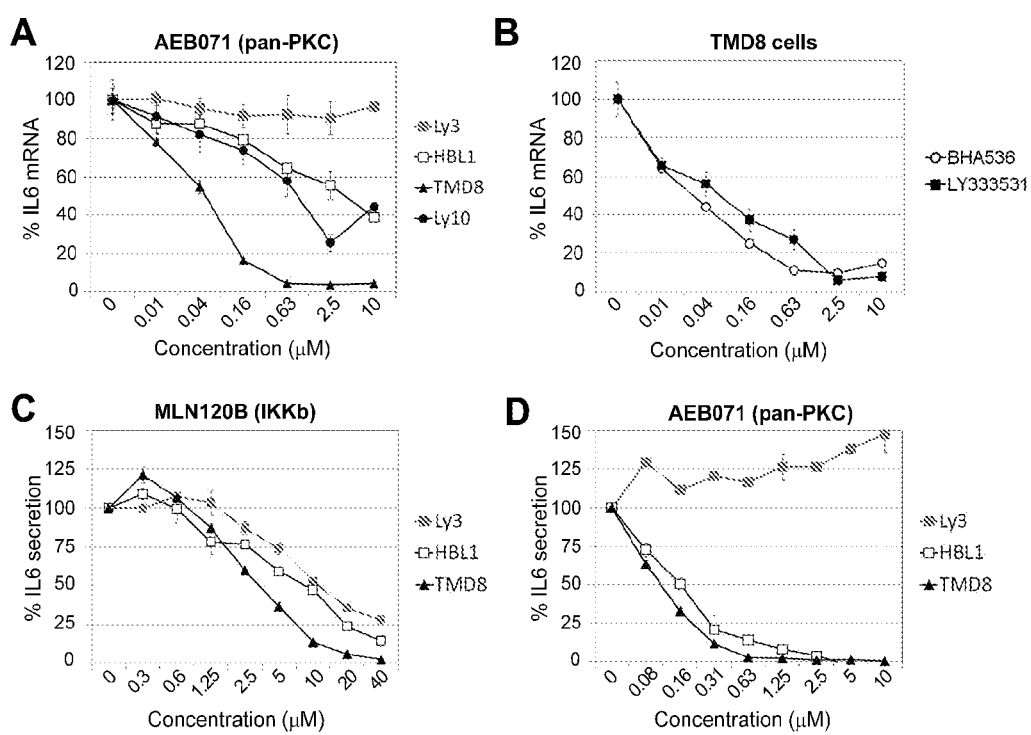
FIG. 2A illustrates the decrease of IL-6 mRNA expression in a dose-dependent manner (in μM) after 24 hours of treatment with the PKC inhibitor, AEB071, in the OCI-Ly3, HBL1, TMD8 and OCI-Ly10 cell lines, where IL-6 mRNA level is expressed as a percentage of IL-6 mRNA level from cells treated with DMSO.
FIG. 2B illustrates the decrease of IL-6 mRNA expression in a dose-dependent manner (in μM) after 24 hours of treatment with the PKC inhibitors, Compound B and LY333531 in the TMD8 cell line, where IL-6 mRNA level is expressed as a percentage of IL-6 mRNA level from cells treated with DMSO.
FIG. 2C illustrates the IL-6 secretion in the OCI-Ly3, HBL1, and TMD8 cell lines after 24 hours of treatment with the IKKb inhibitor, MLN120B, at concentrations ranging from 0 to 40 μM, where IL-6 secretion is expressed as a percentage of IL-6 secretion from cells treated with DMSO.
FIG. 2D illustrates the IL-6 secretion in the OCI-Ly3, HBL1, and TMD8 cell lines after 24 hours of treatment with the PKC inhibitor, AEB071, at concentrations ranging from 0 to 10 μM, where IL-6 secretion is expressed as a percentage of IL-6 secretion from cells treated with DMSO.

The fact that IL-6 is secreted from cells allowed for monitoring of IL-6 levels in cell supernatants. IL-6 secretion was determined by Quantikine ELISA using supernatant from treated cells. Cells were washed and plated at 100,000 cells/well in 100 ul in fresh media in round-bottom 96-well plates (Corning, #3358). The cells were then treated with DMSO or inhibitors at concentrations ranging from 80 nM to 10 uM (2-fold dilutions), and incubated at 37° C. for 48 hours. Then the conditioned media was transferred to v-bottom 96-well plates (Nunc, #12565436). The level of IL-6 secretion was determined by the Quantkine colorimetric ELISA kit from (R & D Systems, #D6050), according to the manufacturer's instructions. For the IL-6 ELISA, the conditioned media was diluted 1:2 with fresh media (except ion: the HBL1 conditioned media was not diluted, it was used 1:1). In FIG. 2, IL-6 secretion for each dose is expressed as a percentage of IL-6 secretion from cells treated with DMSO. Treatment with IKKb inhibitors strongly reduced IL-6 secretion in all ABC DLBCL cell lines tested (FIG. 2C). IL-6 secretion was strongly inhibited by the PKC inhibitors AEB071 and Compound B ($IC_{50}$<0.2 uM) in TMD8 and HBL1 cells. Notably, the PKC inhibitors had no effect on IL-6 (and IL-10) secretion in the CARD11-mutant cell line OCI-Ly3, which correlates with the insensitivity of these cells to PKC inhibitors in the growth assays (FIG. 2D). Importantly, the concentrations required to inhibit NFkB signaling (as measured by IL-6 secretion) in the sensitive lines correlated well with the $IC_{50}$s in the growth inhibitory assays, thus demonstrating that the growth inhibitory effect of PKC inhibitors is mediated by NFkB pathway inhibition.

The OCI-LY10 and OCI-LY3 cell lines were obtained from Dr. Mark Minden's lab (University of Toronto, Canada). HBL1 and TMD8 cells were obtained from Dr. Martin Dyer (University of Leicester, UK) and Dr. Georg Lenz (Charite Berlin, Germany), respectively. DB cells were obtained from ATCC (USA) and U2392, K422, and SU-DHL4 from DSMZ (Germany).

Figure 3A:
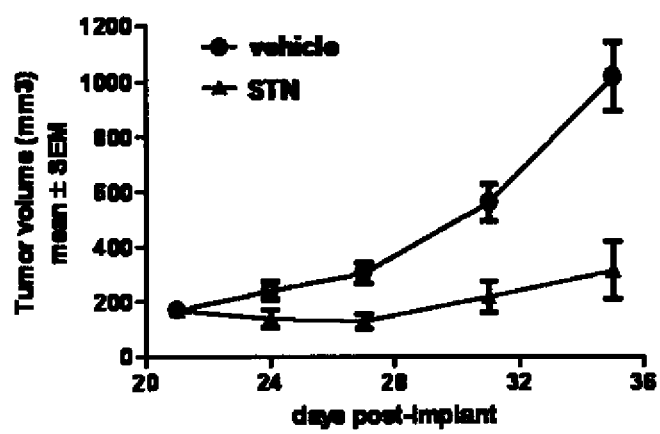
FIG. 3A and FIG. 3B illustrate the inhibition of tumor growth in a TMD8 xenograft mouse model when treated with the PKC inhibitor, AEB071, in vivo.
Figure 3B:
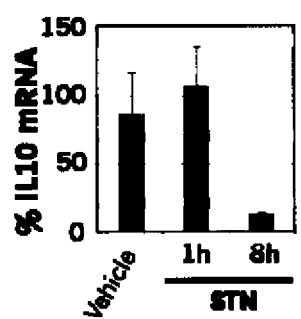

Sensitivity of CD79 Mutant ABC DLBCL to PKC Inhibition In Vivo:

CD79 mutant ABC DLBCL were also shown to be sensitive to PKC inhibition in an in vivo setting by using a subcutaneous TMD8 xenograft model. Female SCID-beige mice were purchased from Charles River Labs (Wilmington Mass.) and housed in temperature and a humidity-controlled vivarium with a 12 hours light cycle and provided food and water ad libitum. Mice were implanted subcutaneously with $10 \times 10^6$ TMD8 cells in 50% matrigel (BD Biosciences, #354234) in the right dorsal axillary region, and animals were randomized into treatment groups when tumor sizes average ~160 mm³ (21 days post-implantation). AEB071 was formulated in 20% PEG400 and 4.5% 0.1 M HCl in D5W. Tumor volume was measured by callipering in 2 dimensions and calculated as (Length×Width²)/2. Animals were callipered twice weekly during treatment to monitor effects on tumor growth. Daily oral dosing of AEB071 (80 mg/kg, tid) resulted in significant inhibition of tumor growth compared to vehicle-treated animals with a T/C of 17%, p<0.05 (see, FIG. 3A). T/C percentage was calculated as the mean change in tumor volumes of treated animals divided by the mean change in tumor volumes of vehicle animals and multiplied by 100. Data are expressed as mean±SEM, and differences are considered statistically significant at p<0.05 by Student t-test.

To confirm that the growth inhibitory effect in response to PKC inhibition is mediated through modulation of NFkB pathway signaling, the mRNA expression of IL-10 was monitored in response to AEB071 treatment in a PD arm of the in vivo study. Mice were implanted with TMD8 cells as described above, and when the tumor volume reached ~160 mm³, a single dose of 80 mg/kg AEB071 was administered. Tumor samples were harvested and snap frozen in liquid nitrogen, at 1 hour or 8 hours following the single does of AEB071. Tissue samples were homogenized and lysed in RLT buffer (Qiagen, #74104) with Reagent DX (Qiagen, 19088) using the TissueLyser II (Qiagen, 85300). Total RNA was harvested using the RNeasy kit (Qiagen, #74104) and cDNA was made from 1 μg total RNA using the High Capacity cDNA kit (ABI, #4368814), according to manufacturer's protocols. The IL-10 Taqman probe (ABI, Hs00174086_m1) was used with Gene Expression Master Mix (ABI, 4369510) to determine the amount of mRNA expression for IL-10 relative to an endogenous control gene (ABI: TBP, 4326322E) and the DMSO control using the delta-delta $C_t$ method.

AEB071 treatment resulted in a decrease in IL-10 mRNA expression in the xenograft tumor tissue after 8 hours of treatment. Consistent with the in vitro kinetics of NFkB target gene downregulation by AEB071, IL-10 mRNA expression was unaffected after just 1 hour of treatment (see, FIG. 3A).

Synergy Between a PKC Inhibitor and mTOR Inhibitor

Figure 4:
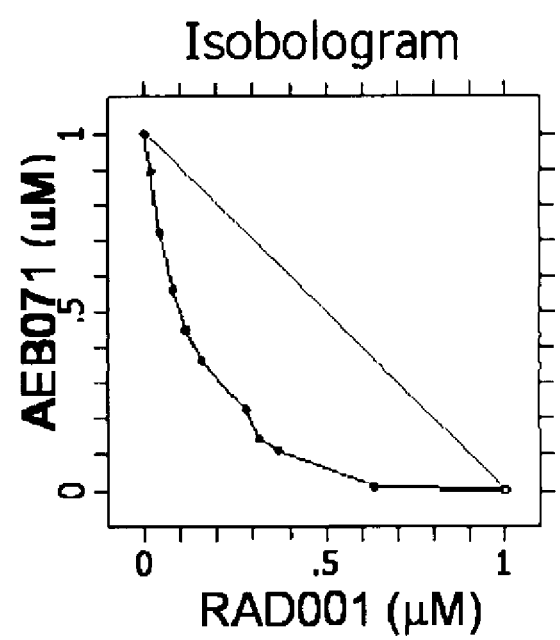
FIG. 4 illustrates the synergy between the PKC inhibitor, AEB071, and the mTOR inhibitor, RAD001, in the CD79 mutant ABC DLBCL cell line TMD8 in vitro.

The pan-PKC inhibitor, Sotrastaurin (also known as AEB071), and the mTOR-selective inhibitor RAD001 were used in combination to demonstrate the proliferation of the CD79 mutant ABC DLBCL line TMD8 in vitro. Cells were plated in 96-well plates (Corning, #3358) at 5000 cells/well in 100 µL and treated in a 6×6 matrix with 12 µL each of inhibitor or DMSO at 10× concentration (final concentrations range from 63 nM to 1 µM for AEB071, and from 3 nM to 50 nM for RAD001; 2-fold dilutions). Following 5 days of treatment, cells were lysed with CellTiter-Glo® Luminescent Cell Viability Assay reagent (Promega, G7573), lysates were transferred to opaque 96-well plates (Corning, #3971), and luminescence signal was read using the Envision. Data were analyzed using Chalice software (licensed from CombinatoRx). Percent inhibition values for the 6×6 dose matrix of AEB071 and RAD001 were calculated relative to DMSO signal). Synergy was determined by comparing the combination's response to those of the single agents. Loewe additivity, also called "dose additivity", describes the trade-off between two agents when both sides of a dose matrix contain the same compound. The ADD Excess Inhibition plot of the dose matrix for AEB071 and RAD001 showed the inhibition above what is expected for two compounds which have an additive effect when combined. A representative isobologram for 60% inhibition was used to graphically illustrate the synergy of AEB071 and RAD001 in combination relative to Loewe additivity. The isobologram compares doses needed to reach 60% inhibition along an equal effect contour to those along a predicted contour based on a model of dose-additivity (represented by the straight diagonal line) (see, FIG. 4). Synergy can be measured in terms of a Combination Index (CI), which is defined as the total ratio of drug required in combination to achieve a given inhibition level over the corresponding single agent concentrations. The combination of AEB071 and RAD001 shows synergy with a $CI_{60}=0.459$ ($CI_{50}=0.704$) in the TMD8 cell line. This finding supports the rational combination of a PKC inhibitor and an mTOR selective inhibitor in settings of chronic BCR pathway activation, including CD79A/B mutated DLBCL.

Pharmaceutical Compositions

For use in the present invention, the PKC inhibitors are generally formulated into a pharmaceutical composition prior to administration. Therefore, another aspect of the present invention is the preparation of a medicament comprising a PKC inhibitor and one or more pharmaceutically acceptable carriers. The pharmaceutical compositions are prepared by procedures well-known to those of skill in the art.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a PKC inhibitor refers to an amount of the PKC inhibitor that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of PKC inhibitor, when administered to a subject, is effective to (1) at least partially alleviating, inhibiting, preventing and/or ameliorating a condition, or a disorder or a disease mediated by the inhibition of the growth of B-cell lymphoma having chronic active B-cell-receptor signaling (preferably, a CD79 mutant diffuse-large B-cell lymphoma), or (ii) associated with such activity, or (iii) characterized by activity (normal or abnormal) of such inhibition; or (2) reducing or inhibiting the growth of B-cell lymphoma having chronic active B-cell-receptor signaling (preferably, a CD79 mutant diffuse-large B-cell lymphoma).

As used herein, the term "a therapeutically effective amount" refers to the amount of the compound of the present invention that, when administered to a cell, or a tissue, or a non-cellular biological material, or a medium, is effective to at least partially reducing or inhibiting the growth of B-cell lymphoma having chronic active B-cell-receptor signaling (preferably, a CD79 mutant diffuse-large B-cell lymphoma).

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder, refers (i) to ameliorating the disease or disorder (i.e., slowing or arresting or reducing the development of the disease or at least one of the clinical symptoms thereof; (ii) to alleviating or ameliorating at least one physical parameter including those which may not be discernible by the patient; (iii) to modulating the disease or disorder, either physically, (e.g., stabilization of a discernible symptom), physiologically, (e.g., stabilization of a physical parameter), or both; or (iv) to preventing or delaying the onset or development or progression of the disease or disorder. In general, the term "treating" or "treatment" describes the management and care of a patient for the purpose of combating the disease, condition, or disorder and includes the administration of a PKC inhibitor to prevent the onset of the symptoms or complications, alleviating the symptoms or complications, or eliminating the disease, condition or disorder.

As used herein, a subject is "in need of" a treatment if such subject would benefit biologically, medically or in quality of life from such treatment (preferably a human).

Another aspect of the present invention provides the use of a PKC inhibitor, in the manufacture of a medicament for the treatment of a disorder or disease in a subject characterized by the inhibition of the growth of B-cell lymphoma having chronic active B-cell-receptor signaling (preferably, a CD79 mutant diffuse-large B-cell lymphoma) or the inhibition of the growth of cancers with molecular lesions that lead to chronic active BCR signaling.

The pharmaceutical composition can be formulated for particular routes of administration such as oral administration, parenteral administration, and rectal administration, etc.

In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and/or
  e) absorbents, colorants, flavors and sweeteners.

Tablets may be either film coated or enteric coated according to methods known in the art.

Suitable compositions for oral administration include an effective amount of a PKC inhibitor in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a PKC inhibitor with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

In certain instances, it may be advantageous to administer the PKC inhibitor in combination with an additional anti-cancer agent or adjunct therapy typically used in chemotherapy. The PKC inhibitor may be administered either simultaneously with, or before or after, one or more other therapeutic agent(s). The PKC inhibitor may be administered separately, by the same or different route of administration, or together in the same pharmaceutical composition as the other agent(s). For example, the PKC inhibitor may be added to the current standard of care which includes a combined therapy with anti-CD20 antibody rituximab and chemotherapy for the treatment of non-Hodgkin lymphoma (also referred to as R-CHOP). Other suitable additional anti-cancer agents include mTOR inhibitors, PI3K inhibitors and JAK inhibitors.

Suitable mTOR inhibitors include Temsirolimus (sold under the tradename Torisel® by Pfizer), ridaforolimus (formally known as deferolimus, (1R,2R,4S)-4-[(2R)-2[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669, and described in PCT Publication No. WO 03/064383), everolimus (sold under the tradename Afinitor® by Novartis and also referred to as "RAD001"), Rapamycin (sirolimus), OSI-027 (OSI Pharmaceuticals), and compounds described in WO 06/090167; WO 06/090169; WO 07/080,382, WO 07/060,404; and WO 08/023,161. A particularly useful mTOR inhibitor is everolimus (RAD001).

Suitable PI3K inhibitors include wortmannin, 17-hydroxy-wortmannin analogs described in WO 06/044453, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quino-lin-1-yl]phenyl]propionitrile (also known as BEZ 235 or NVP-BEZ 235, and described in PCT Publication No. WO 06/122806), (S)-1-(4-((2-(2-aminopyrimidin-5-yl)-7-me-thyl-4-morpholinothieno[3,2-d]pyrimidin-6-yl)methyl)pip-erazin-1-yl)-2-hydroxypropan-1-one (described in PCT Publication No. WO 2008/070740), LY294002 (2-(4-Morpholinyl)-8-phenyl-4H-1-benzopyran-4-one available from Axon Medchem), PI 103 hydrochloride (3-[4-(4-mor-pholinylpyrido-[3',2':4,5]furo[3,2-d]pyrimidin-2-yl]phenol hydrochloride available from Axon Medchem), PIK 75 (N'-[(1E)-(6-bromoimidazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydro-imidazo[1,2-c]quinazolin-5-yl)-nicotinamide available from Axon Medchem), GDC-0941 bismesylate (2-(1H-Indazol-4-yl)-6-(4-methanesulfonyl-piperazin-1-ylm-ethyl)-4-morpholin-4-yl-thieno[3,2-d]pyrimidine bismesy-late available from Axon Medchem), AS-252424 (5-[1-[5-(4-Fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[1-(phenylamino) ethyl]-4H-pyrido-[1,2-a]pyrimidin-4-one available from Axon Medchem), XL-765, and XL-147.

Suitable janus-associated kinase (JAK) inhibitors (e.g., JAK1, JAK2 or JAK3 inhibitors) include (R)-3-(4-(7H-pyr-rolo[2,3-d]pyrimidin-4-yl)-1H-pyrazol-1-yl)-3-cyclopentyl-propanenitrile (also referred to as INCB018424 and described by Lin, Z., et al., in *Organic Letters* "Enantioselec-tive Synthesis of Janus Kinase Inhibitor INCB018424 via an Organocatalytic Aza-Michael Reaction" 11(9), 1999-2002 (2009)), and N-(1,1-dimethylethyl)-3-[[5-methyl-2-[[4-[2-(1-pyrrolidinyl)ethoxy]phenyl]amino]-4-pyrimidinyl] amino]benzenesulfonamide (also referred to as TG101348 and described in PCT Publication No. WO 2007/053452), N-[4-[[4-(4-methylpiperazin-1-yl)-6-(5-methyl-2H-pyrazol-3-ylamino)pyrimidin-2-yl]sulfanyl]phenyl]amide cyclopro-panecarboxylic acid (also known as MK 0457, Tozasertib and VX 680), 2,3,9,10,11,12-hexahydro-10-hydroxy-10-(hy-droxymethyl)-9-methyl-[9S-(9α,10β,12α)]-9,12-epoxy-1H-diindolo[1,2,3-fg:3',2',1'-kl]pyrrolo[3,4-i][1,6]benzodiazo-cin-1-one (also known as CEP 701 and Lestaurtinib), 3-((3R, 4R)-4-methyl-3-(methyl(7H-pyrrolo[2,3-d]pyrimidin-4-yl) amino)piperidin-1-yl)-3-oxopropanenitrile (also known as CP-690550), (N-(cyanomethyl)-4-[2-[[4-(4-morpholinyl) phenyl]amino]-4-pyrimidinyl]-benzamide (also referred to as CYT387 and described in Burns, C. J., et al., *Bioorg Med Chem Lett* 19, 5887-5892 (2009)), XL-019 (CAS #1123889-86-0), SB-1518 (CAS #1138325-13-0), and compounds disclosed in PCT Publication Nos. WO 08/148,867 and WO 07/071,393. Preferably, the JAK inhibitors are selective JAK2 inhibitors, selective JAK1 and/or JAK2 inhibitors, selective JAK1 and/or JAK3 inhibitors, or selective JAK2 and/or TYK2 inhibitors.

Another aspect of the invention is a product comprising a PKC inhibitor and at least one other therapeutic agent (or pharmaceutical agent) as a combined preparation for simultaneous, separate or sequential use in therapy to inhibit the growth of B-cell lymphoma having chronic active B-cell-receptor signaling (preferably, a CD79 mutant diffuse-large B-cell lymphoma (e.g., non-Hodgkin's lymphoma)) or to inhibit the growth of cancers with molecular lesions that lead to chronic active BCR signaling.

In the combination therapies of the invention, the PKC inhibitor and the other therapeutic agent may be manufactured and/or formulated by the same or different manufacturers. Moreover, the PKC inhibitor and the other therapeutic (or pharmaceutical agent) may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a PKC inhibitor for treating a disease or condition mediated by inhibiting the growth of B-cell lymphoma having chronic active B-cell-receptor signaling (preferably, a CD79 mutant diffuse-large B-cell lymphoma (e.g., non-Hodgkin's lymphoma)) or to inhibit the growth of cancers with molecular lesions that lead to chronic active BCR signaling, wherein the medicament is prepared for administration with another therapeutic agent. The invention also provides the use of another therapeutic agent for treating a disease or condition mediated by inhibiting the growth of B-cell lymphoma having chronic active B-cell-receptor signaling (preferably, a CD79 mutant diffuse-large B-cell lymphoma (e.g., non-Hodgkin's lymphoma)) or to inhibit the growth of cancers with molecular lesions that lead to chronic active BCR signaling, wherein the medicament is administered with a PKC inhibitor.

What is claimed is:
1. A method for inhibiting the growth of B-cell lymphoma having chronic active B-cell-receptor signaling comprising administering to a patient in need of such treatment
   (i) a PKC inhibitor selected from the group consisting of sotrastaurin, 3-(1H-Indol-3-yl)-4-[2-(piperazin-1-yl) quinazolin-4-yl]-1H-pyrrole-2,5-dione; 3-[2-chloro-7-[(dimethylamino)methyl]-1-naphthalenyl]-4-[7-[2-(2-methoxyethoxy)ethoxy]-1H-indol-3-yl]-1H-pyrrole-2, 5-dione; 3-[3-(4,7-diaza-spiro[2,5]oct-7-yl)-isoquinolin-1-yl]-4-(7-methyl-1H-indol-3-yl)-pyrrole-2,5-dione; 3-[2-chloro-7-[(dimethylamino)methyl]-1-naphthalenyl]-4-[7-[2-(2-methoxyethoxy)ethoxy]-1H-indol-3-yl]-1H-pyrrole-2,5-dione; and (9S)-9-[(dimethylamino)methyl]-6,7,10,11-tetrahydro-9H,

18H-5, 21:12,17-dimethenodibenzo[e,k]pyrrolo[3,4-h][1,4,13]oxadiazacyclohexadecine-18,20(19H)-dione; and (ii) an mTOR inhibitor which is everolimus.

2. The method of claim 1 wherein said PKC inhibitor and said mTOR inhibitor are administered simultaneously.

3. The method of claim 1 wherein said PKC inhibitor and said mTOR inhibitor are administered sequentially.

4. The method of claim 1, 2, or 3 wherein said PKC inhibitor is sotrastaurin.

5. A method for inhibiting the growth of B-cell lymphoma having chronic active B-cell-receptor signaling comprising administering to a patient in need of such treatment
(i) sotrastaurin and
(ii) everolimus.

6. The method of claim 4 wherein said B-cell lymphoma having chronic active B-cell receptor signaling is a CD79 mutant diffuse-large B-cell lymphoma.

7. The method of claim 5 wherein said B-cell lymphoma having chronic active B-cell receptor signaling is a CD79 mutant diffuse-large B-cell lymphoma.

\* \* \* \* \*